United States Patent [19]

Pereira et al.

[11] Patent Number: 5,322,936
[45] Date of Patent: Jun. 21, 1994

[54] NUCLEIC ACIDS ENCODING TRYPANOSOMA CRUZI HEPARIN-BINDING PROTEIN

[75] Inventors: Miercio E. A. Pereira, Chestnut Hill; Eduardo Ortega-Barria, Brighton, both of Mass.

[73] Assignee: New England Medical Center Hospitals, Inc., Boston, Mass.

[21] Appl. No.: 104,503

[22] Filed: Aug. 6, 1993

Related U.S. Application Data

[62] Division of Ser. No. 779,706, Oct. 17, 1993, Pat. No. 5,234,822.

[51] Int. Cl.⁵ .............................................. C07H 21/04
[52] U.S. Cl. ................................... 536/23.5; 530/350; 435/69.1; 435/172.1; 435/240.1; 435/252.3; 435/320.1; 424/88
[58] Field of Search ................. 536/23.5, 23.7; 935/9; 530/387, 350; 424/85.8, 88; 435/69.1-69.3, 172.1, 240.1, 252.3, 320.1; 514/12

[56] References Cited

U.S. PATENT DOCUMENTS 4,870,006  9/1989  Dragon et al. .......................... 435/7

OTHER PUBLICATIONS

Hudson, Phil. Trans. R. Soc. Lond., vol. 307, issued 1984, pp. 51–61.
Ortega-Barria et al. Cell:67:411–421 Oct. 18, 1991.
Schenkman et al., Cell 55:157 1988.
Ouassi et al Science 234:603 1986.
Ouassi et al Mol. Biochem. Parasitol. 19:201, 1986.
Velge et al Parasitology 97:255 1988.
Pnoli et al Mol. Biochem. Parasitol 38:191 1990.
Isberg et al Science 252:934, 1991.
Pereira et al. J. Exp. Med. 174:179 1991.
Hernandez et al. Mol. Biochem. Parasitol. 41:207–217 1990.

Primary Examiner—Robert J. Hill, Jr.
Assistant Examiner—Lorraine M. Spector
Attorney, Agent, or Firm—Fish & Richardson

[57] ABSTRACT

Disclosed is recombinant penetrin polypeptide. Also disclosed is nucleic acid encoding penetrin, recombinant cells and plasmids encoding penetrin, antibodies directed against penetrin and various uses for penetrin and antibodies directed against penetrin.

9 Claims, 11 Drawing Sheets 1  2

NUCLEIC ACIDS ENCODING TRYPANOSOMA CRUZI HEPARIN-BINDING PROTEIN

This invention was made with Government support under Grant No. AI18102 awarded by the PHS. The Government has certain rights in the invention.

This is a divisional of copending application Ser. No. 07/779,706, filed Oct. 17, 1993, issued Aug. 10, 1993 as U.S. Pat. No. 5,234,822.

BACKGROUND OF THE INVENTION

*Trypanosoma cruzi*, a parasitic protozoan, is the causative agent of Chagas' disease, a multisystemic disorder that affects millions of people in Latin America. *T. cruzi* exists in three distinct developmental forms: epimastigotes, which multiply extracellularly in the midgut of reduviid bugs; amastigotes, which multiply inside mammalian cells; and trypomastigotes, which transmit infection from insects to man and vice-versa, but which do not multiply Trypomastigotes must travel through the bloodstream, cross the vascular epithelium, and migrate through the extracellular matrix to reach the cells of the organs which *T. cruzi* infects. Once they have entered host cells, trypomastigotes transform into amastigotes which multiply and eventually transform back into trypomastigotes which can exit the host cell and migrate through the interstitial tissue to invade other cells.

Receptor-ligand interactions may play a role in *T. cruzi* invasion of cells. Ouaissi et al. (Science 234:603, 1986) report that peptides modeled on a protein, fibronectin, present on host cells can inhibit *T. cruzi* infection in vitro. Ouaissi et al. (*Mol. and Biochem. Parasitol.* 19:201, 1986) report the identification and isolation 80-85 kD trypomastigote cell surface protein with properties expected of a fibronectin receptor. Velge et al. (*Parasitology* 97:255, 1988) report the isolation of a *T. Cruzi* trypomastigote collagen-binding protein. When analyzed by polyacrylamide gel electrophoresis, the protein migrates as a 58 kD protein under non-reducing conditions and as a 68 kD protein under reducing conditions. Velge et al. also identify an 80-85 kD protein which reacts with antibodies raised against the 68/58 kD protein; they suggest that both the 80-85 kD and the 58/68 kD glycoproteins form part of the same receptor.

SUMMARY OF THE INVENTION

In general, the invention features recombinant penetrin polypeptide. Preferably, the polypeptide is derived from *T. cruzi*. Preferably such polypeptides have at least 70%, more preferably at least 80%, even more preferably at least 90% homology to the penetrin of *T. cruzi*. By "derived from" is meant encoded by the genome of that organism.

The invention further features a substantially pure polypeptide which is a fragment or analog of penetrin capable of inhibiting *T. cruzi* infection of a eukaryotic cell. A *T. cruzi* infection inhibiting fragment can be identified using an assay described herein below. In this assay Vero cells are exposed to *T. cruzi* in the presence and absence of putative inhibitors and infection rates are measured. Portions of penetrin which are exposed on the surface of trypomastigotes are likely to be better inhibitors than non-exposed portions.

The invention also features a substantially pure polypeptide which is a fragment or analog of penetrin capable of promoting adhesion of eukaryotic cells to a solid support surface.

By "penetrin polypeptide" is meant all or part of a trypomastigote cell surface protein which promotes adhesion to and penetration of eukaryotic cells. By "polypeptide" is meant any chain of amino acids, regardless of length or post-translational modification (e.g., glycosylation). Preferably a polypeptide includes at least 10, more preferably at least 15, even more preferably at least 20, and even more preferably at least 30 amino acids.

In a related aspect, the invention features an isolated nucleic acid which encodes a penetrin polypeptide (or fragment or analog thereof) described above. Preferably such nucleic acids have at least 70%, more preferably at lest 80%, even more preferably at least 90% homology to the penetrin encoding gene of *T. cruzi*. In a preferred embodiment, the nucleic acid includes a sequence substantially identical to the penetrin encoding portion of the DNA molecule identified as HBD-6, deposited with the ATCC and given Accession No. ATCC 75126. By "substantially identical" nucleic acid sequence is meant a sequence capable of encoding a substantially identical amino acid sequence.

In a related aspect, the invention features a plasmid which includes an isolated nucleic acid described above. In a preferred embodiment, the plasmid includes an expression control sequence capable of directing expression of the penetrin polypeptide.

In a related aspect, the invention features a cell which includes an isolated nucleic acid described above. In various preferred embodiments, the cell is a prokaryotic cell; is a eukaryotic cell; and is a mammalian cell.

In another aspect, the invention features penetrin produced by a cell described above.

In another aspect, the invention features a purified antibody which is capable of forming a specific immune complex with a penetrin polypeptide (or fragment or analog thereof). By "purified antibody" is meant one which is sufficiently free of other proteins, carbohydrates, and lipids with which it is naturally associated to permit therapeutic administration or use in ELISA-type assays of biological fluids.

In another aspect, the invention features a polypeptide which includes an amino acid sequence substantially identical to that encoded by the penetrin coding portion of the DNA molecule identified as HBp-6 deposited with the ATCC and given Accession No. ATCC-75126. By a "substantially identical" amino acid sequence is meant an amino acid sequence which differs only by conservative amino acid substitutions, for example, substitution of one amino acid for another of the same class (e.g., valine for glycine, arginine for lysine, etc.) or by one or more non-conservative amino acid substitutions, deletions, or insertions located at positions of the amino acid sequence which do not destroy the biological activity of the penetrin polypeptide.

In another aspect, the invention features a therapeutic composition which includes, in a pharmaceutically acceptable carrier, a substantially pure penetrin polypeptide (or fragment or analog thereof) as described above.

In another aspect, the invention features a method of detecting penetrin in a sample of biological fluid. The method includes: (a) contacting the sample of biological fluid with an antibody described above; and (b) detecting immune complexes formed in step (a), formation of immune complexes being an indication of the presence of *T. cruzi* penetrin in the biological fluid.

In another aspect, the invention features a method of detecting an antibody reactive with penetrin in a sample of biological fluid. The method includes (a) contacting the sample of biological fluid with a substantially pure penetrin polypeptide or an immunogenic fragment thereof; and (b) detecting immune complexes formed in step (a), formation of the immune complexes being an indication of the presence of the antibody reactive with penetrin in the biological fluid.

In another aspect, the invention features a solid support surface for growing eukaryotic cells, the surface being coated with penetrin. Solid support surfaces for growing eukaryotic cells include: roller bottles, tissue culture plates, hollow fiber filter systems, and the like. Such surfaces can be coated with penetrin in much the same way as they are coated with fibronectin.

In yet another aspect, the invention features a vaccine which includes a substantially pure penetrin polypeptide or immunogenic fragment thereof.

By "isolated" is meant that the nucleic acid is largely free of the coding sequences of those genes that, in the naturally occurring genome of the organism from which the nucleic acid is derived, directly flank the nucleic acid. Isolated nucleic acid may be genomic DNA, cDNA, chemically synthesized nucleic acid, enzymatically synthesized nucleic acid, or recombinant nucleic acid. The term includes chemically and enzymatically synthesized nucleic acid produced using a recombinant nucleic acid as a template. By "plasmid" is meant an extrachromosal DNA molecule which includes sequences that permit replication within a particular host cell. By "expression control sequence" is meant a nucleotide sequence which includes recognition sequences for factors that control expression of a protein coding sequence to which it is operably linked. Accordingly, an expression control sequence generally includes sequences for controlling both transcription and translation, for example, promoters, ribosome binding sites, repressor binding sites, and activator binding sites. "Homology" for amino acid sequences refers to the similarity between two or more amino acid sequences. The percent homology of two given proteins is determined using sequence analysis software (e.g., the Sequence Analysis Software Package of the Genetics Computer Group, University of Wisconsin, Madison, Wis.). Such software determines the homology of two amino acid sequences that have been aligned so as to maximize homology. Homology values are assigned to exact matches as well as certain types of conservative amino acid substitutions. Such conservative substitutions include replacement of one acidic amino acid by another acidic amino acido. For nucleic acid homology is the percent identity between optimally aligned sequences.

By "substantially pure" is meant a polypeptide or protein which has been separated from components (e.g., other proteins) with which it is normally found. Typically, a protein or polypeptide of interest is substantially pure when at least 75% (preferably 85%) of the polypeptide in a sample is the protein or polypeptide of interest. By the term "capable of forming a specific immune complex" is meant an antibody does not substantially bind other molecules.

Besides substantially full-length penetrin, the present invention provides biologically active fragments of penetrin. As used herein, the term "fragment", as applied to penetrin, will ordinarily be about 5 contiguous amino acids, typically at least 10 contiguous amino acids, preferably at least 15 amino acids, and most preferably at least 20 amino acids.

Other features and advantages of the invention will be apparent from the following description of the preferred embodiments thereof, and from the claims.

DETAILED DESCRIPTION

The drawings are first briefly described.

DRAWINGS

FIGS. 1A and B depict a pair of graphs illustrating the adherence of [$^{35}$S]-labeled trypomastigotes to various materials. In panel A, trypomastigote bound (cpm $\times 10^{-3}$) to microtiter wells coated with 25 μg/ml heparin are plotted as a function of the incubation time (min). In panel B, trypomastigote bound (cpm $\times 10^{-3}$) to microtiter wells coated with 25 μg/ml heparin are plotted as a function of the number of trypomastigote ($\times 10^{-4}$) added to the microtiter well.

FIG. 2 is a graphical representation of the effect of the concentration (μg/ml) of heparin (filled squares), heparan sulfate (filled circles), collagen IV (open squares), hyaluronic acid (filled diamonds), or chondroitin sulfate (squares with central dot) bound to microtiter wells on binding of [$^{35}$S]-labeled trypomastigote (cpm $\times 10^{-4}$) bound.

FIGS. 3A and B depict a pair of graphs illustrating the adherence of trypomastigotes to Vero cells. [$^{35}$S]-labeled trypomastigote bound (cpm $\times 10^{-4}$) are plotted as a function of incubation time (min) in panel A and as a function of trypomastigote added ($\times 10^{-5}$) in panel B.

FIG. 4 is a graphical representation of the effect of the concentration (μg/ml) of heparan sulfate (open circles), heparin (filled circles), chondroitin sulfate (open squares), or hyaluronic acid (filled squares) on inhibition of Vero cell infection (%).

FIG. 5 is a representation of an SDS-PAGE analysis of [$^{125}$I]-labeled proteins in trypomastigote lysate (lane 1), 1.0M NaCl eluate (lane 2), and effluent from a heparin-Sepharose column (lane 3).

FIG. 6 is a representation of an immunoblot analysis of trypomastigote (lane 1) and amastigote (lane 2) lysates after 10% SDS-PAGE and transfer to nitrocellulose using mouse anti-penetrin antibodies as a probe. Numbers at left indicate the position of markers having the indicated molecular weight (kD).

T. CRUZI Adhesion Protein

The isolation and cloning of a novel *T. cruzi* adhesion protein, penetrin, is described below. In addition, experiments described below demonstrate that: penetrin binds selectively to proteoglycans and collagen; penetrin promotes the adhesion and spreading of host cells on the substratum; and that penetrin inhibits the ability of T. cruzi trypomastigotes to infect cultured cells. Other experiments demonstrate that when E. coli are made to express penetrin, they are able to adhere to and penetrate non-phagocytic fibroblasts.

T. cruzi

The Silvio X-10/4 clone of T. cruzi (Prioli et al., J. Immunol. 144:4384, 1990) was used in all of the experiments described herein.

Trypomastigotes were obtained by infection of cultured Vero cells as described by Prioli et al. (supra). After harvesting, the parasites were washed three times in serum free RPMI-1640 and resuspended at the desired concentration in phosphate-buffered saline (PBS, 150mM NaCl; 20mM $NaH_2PO_4$, pH 7.2) for radioiodination and competitive binding assays, or in serum-free RPMI-1640 containing 1% BSA for adhesion and infection experiments.

Adherence of T. cruzi Trypomastigotes to Immobilized Proteoglycans

Trypomastigotes adhered to heparin/heparan sulfate, collagen type I and collagen type II that had been immobilized on a plastic surface. In contrast, trypomastigotes bound poorly or not at all to chondroitin sulfate, hyaluronic acid, and the glycoproteins fetuin, asialofetuin, bovine submaxillary mucin, and hog gastric mucin.

For these adhesion experiments trypomastigotes were labeled with [$^{35}$S] methionine as follows. Trypomastigotes ($2 \times 10^8$ cells/ml) were preincubated in methionine-free RPMI 1640 containing 1% dialyzed-FCS. After 1h at 37° C., 250 mCi/ml of [$^{35}$S] methionine (specific activity 1113 Ci/mmole, ICN Biomedicals Inc., Irvine, Calif.) were added, and continued for 60 min at 37° C. The organism were washed three times in RPMI 1640 and adjusted to the appropriate parasite number in the same medium. Incorporation of [$^{35}$S] methionine into T. cruzi, determined by TCA precipitation, was usually about 50%, with a specific activity ranging from 0.5I to 0.71 cpm/organism.

Figure 1A:
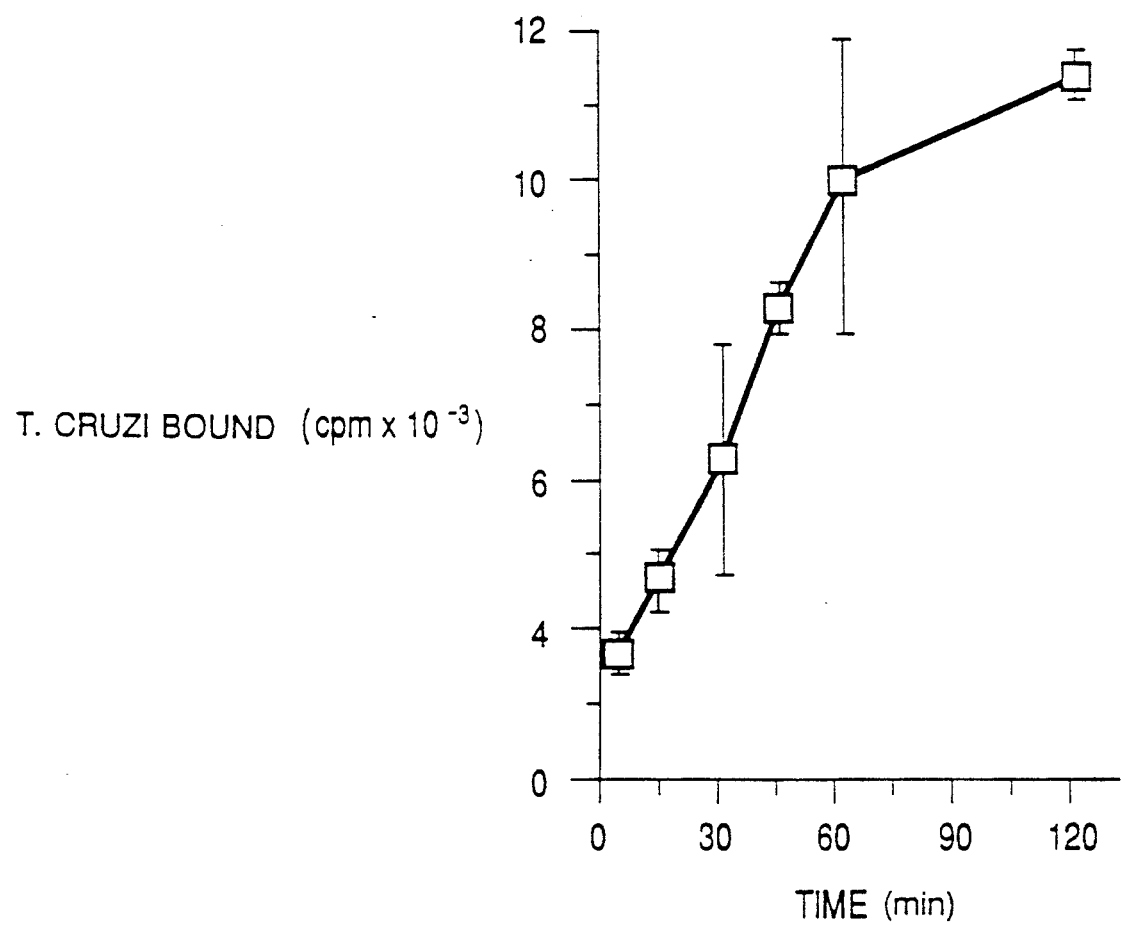
Figure 1B:
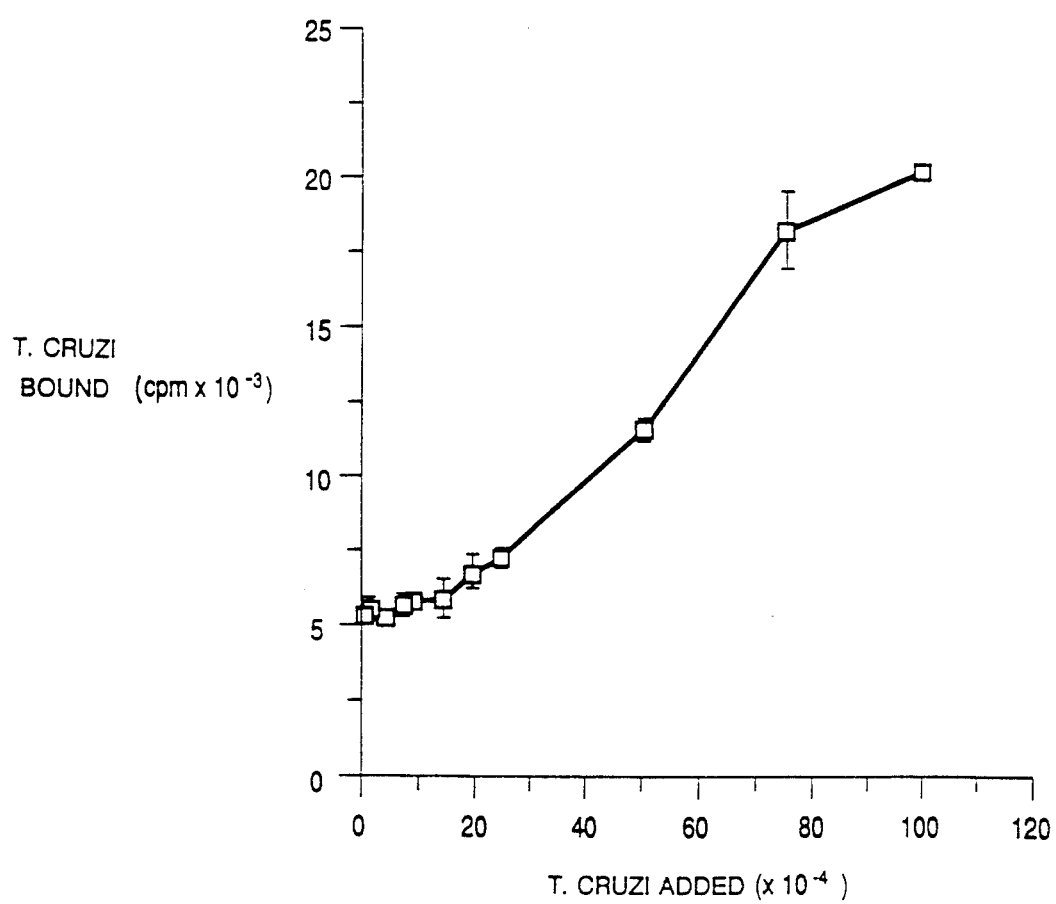

Proteoglycans (dissolved in PBS) and collagen (solubilized in 0.1N HCl and neutralized in PBS) were adsorbed onto plastic (Falcon 3912 polyvinylchloride 96-well microliter plates) by incubation overnight at 4° C (Roberts et al., J. Biol. Chem. 264:9289, 1989). The unbound proteins were removed, the wells filled with 1% heat-treated BSA in PBS (56° C, 60 min and filtered in 0.22 mm nitrocellulose filters to remove insoluble particles) and incubated for 1 h at room temperature. The wells were then washed twice with PBS (pH 7.2) and rinsed with RPMI 1640 containing 1% BSA. T. cruzi trypomastigotes, labeled with [$^{35}$S] methionine, were resuspended in RPMI-BSA and 100 μl of the suspension was applied to the wells. After various periods of incubation at 37° C., the wells were carefully washed three times with 37° C. PBS (pH 7.2). T. cruzi bound to the plastic-bound proteoglycans were then solubilized with 100 μl of 2 M NaOH, mixed with Ultrafluor (National Diagnostics, Manville, N.J.), and assayed by liquid scintillation counting. Referring to FIG. 1a, adherence of trypomastigotes to heparin-coated plates increased linearly with the length of incubation up to about 60 min. In a separate experiment trypomastigotes were added for 60 min, but the number added was varied. This experiment demonstrated that roughly 20–40% of input trypomastigotes remained bound to the heparin coated wells (FIG. 1B). In contrast, nonspecific binding to BSA-coated wells was less than 2%.

Figure 2:
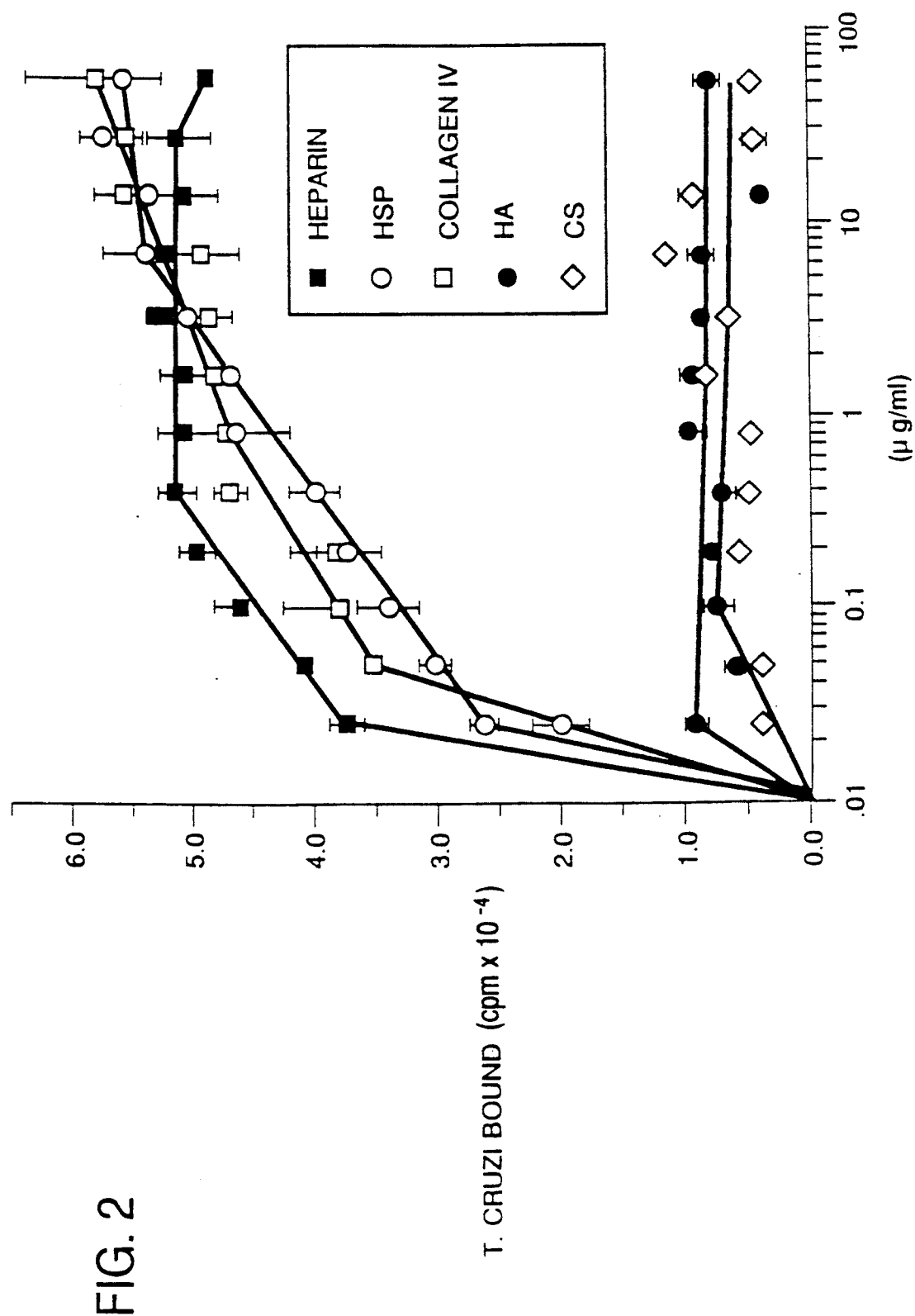

Referring to FIG. 2, heparin (filled squares) heparan sulfate (filled circles), and collagen IV (open squares) were equally effective in promoting trypomastigote adherence. Chondroitin sulfate (squares with central dot) and hyaluronic acid (filled diamonds) did not promote adhesion. A similar set of experiments demonstrated that collagen I, but not fetuin, asialofetuin, bovine submaxillary mucin, or hog gastric mucin promote adhesion. Soluble heparin, soluble heparan sulfate and soluble collagen inhibited trypomastigote binding to heparin- or collagen-coated wells. Proteoglycans Neutralize T. cruzi

Adherence to Vero Cells

The adherence of T. cruzi to glutaraldehyde-fixed fibroblasts (Vero cells) was found to be dose dependent, time dependent and saturable. Low concentrations of heparin or heparan sulfate inhibited adhesion of trypomastigotes to Vero cells. In contrast, incubation with chondroitin sulfate, hyaluronic acid, bovine submaxillary mucin, hog gastric mucin, fetuin, or asialofetuin did not affect adhesion. Preincubation of T. cruzi with heparin or heparan sulfate followed by washing to remove unbound proteoglycans blocked adhesion. Similar treatment of Ver cells prior to incubation with T. cruzi had no effect on adhesion.

In these experiments attachment of trypomastigotes to Vero cell monolayers was measured as follows. Briefly, Vero cells were maintained in RPMI 1640 supplemented with heat-inactivated 1% Nu-serum (Collaborative Research Inc., Bedford, Mass.), penicillin (100 U/ml) and streptomycin (100 mg/ml). Unless noted otherwise, cells were maintained in plastic tissue culture flasks (150 $cm^2$, Bellco, Vineland, N.J.) and incubated at 37° C. in a humidified atmosphere containing 5% $CO_2$ and 95% air. Cells were propagated every 1–2 weeks after trypsin-EDTA digestion (0.5 g trypsin, 0.2 g EDTA in HBSS without $Ca^{++}$ and $Mg^{++}$) in 16-well Lab-Tek ® chamber slide TM (Nunc, Inc., Naperville, Ill. Prior to binding experiments Vero cells were removed with trypsin and plated on 96-well tissue culture plates (Bellco, Vineland, N.J.) or in 16-well Lab-Tek ® chamber slide TM at a density of $7.5 \times 10^3$ cells per well. After 24 h, the medium was removed, cells were washed twice with PBS, pH 7.2, and fixed for 5 min at 4° C. by addition of 2% glutaraldehyde (grade I, Sigma Chemical Co., St. Louis, Mo.) in PBS. Cell monolayers were washed twice with PBS, pH 7.2 and incubated overnight at 4° C. in 0.16M ethanolamine, pH 8.3 to block residual free amino groups. The next day, cell monolayers were washed three times with PBS as above, and two times with 1% BSA/RPMI-1640 and kept at least 1 h at 37° C. in the same medium.

Trypomastigotes, [$^{35}$S]-labeled as described above, were added to the cell monolayers in a total volume of 100 μl well and the plates were incubated for 1 h at 37° C. Each well was then washed five times with 100 μl prewarmed PBS (pH 7.2). The [$^{35}$S] label was solubilized with 2M NaOH and the bound radioactivity was determined in a liquid scintillation counter. Alternatively, unlabeled trypomastigotes were added to wells of a 16-well Lab-Tek ® chamber slide TM and incubated as above. After removing the plastic chamber, the slide was washed by dipping 5 times in PBS (pH 7.2) and immersed upside-down in 4% paraformaldehyde in PBS, containing 7% sucrose. Finally, the slide was rinsed with PBS, stained with Diff-Quik ® and the number of bound T. cruzi were determined by counting under light microscopy. For inhibition studies, trypomastigotes were preincubated 30 min at 37° C. with the appropriate proteoglycan in 100 μl of 1% BSA-RPMI-1640 before addition to cell monolayers. Binding was determined in triplicate at each inhibitor concentration and in the absence of inhibitor.

Figure 3A:
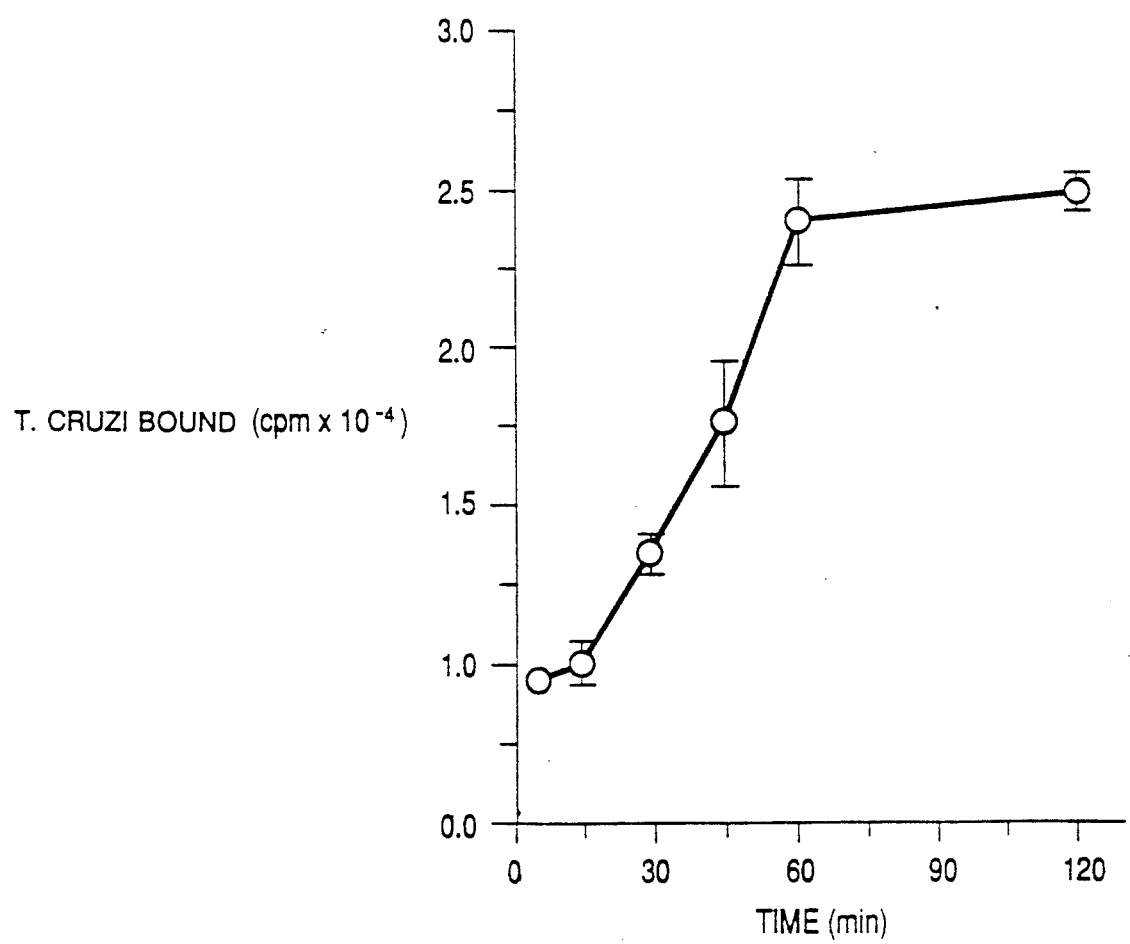
Figure 3B:
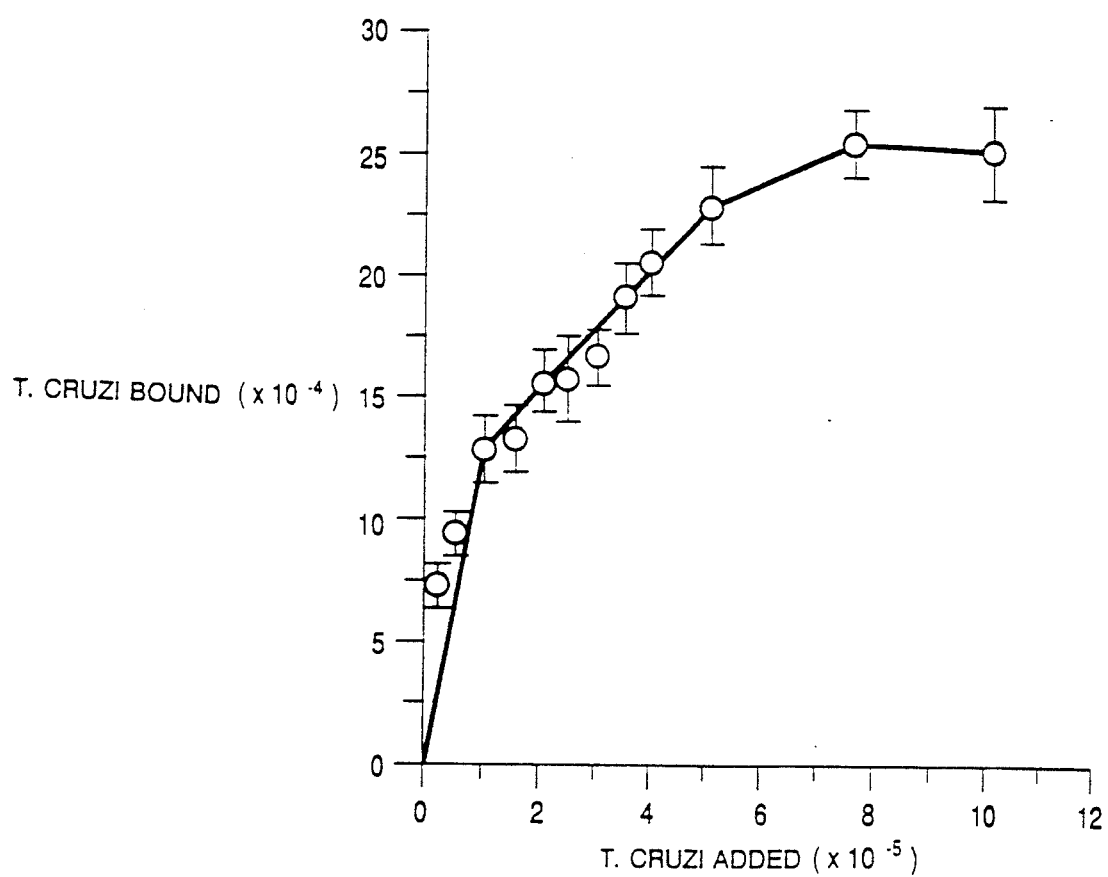

Referring to FIGS. 3A and 3B, binding studies demonstrated that trypomastigote adherence to Vero cells was dependent on incubation time and the number of T. cruzi added. Binding was also shown to be saturable. In these experiments 100% binding was taken as $5 \times 10^5$ trypomastigotes/well for 60 min.

Table 1 presents the results of the binding inhibition assay. In this assay 100% binding was taken to $5 \times 10^4$ trypomastigotes/well bound in 60 min.

TABLE 1

Inhibition of Trypomastigote Binding to Vero Cells

| Inhibitor | Conc. (μg/ml) | % Vero Cells with Trypomastigotes |
|---|---|---|
| BSA | 250 | 95 |
| Heparin | 125 | 50 |
|  | 250 | 12.5 |
| Heparan Sulfate | 125 | 60 |
|  | 250 | 18 |
| Hyaluronic Acid | 250 | 98 |
| Chonodroitin Sulfate | 250 | 96 |
| Bovine Submaxillary Mucin | 250 | 96 |

These results are consistent with the existence of a heparin-binding ligand(s) on T. cruzi that mediates adherence by recognizing heparin-like receptor(s) on the surface of fibroblasts.

Inhibition of T. cruzi Infection by Heparin and Heparan Sulfate

Both soluble heparin and heparan sulfate inhibited infection of Vero cells by trypomastigotes whereas chondroitin sulfate and hyaluronic acid had little effect on infection. Incubation of Vero cells with heparin or heparan sulfate followed by washing had no effect on infection.

In these experiments, cultured Vero cells were released with trypsin/EDTA, plated at $7.5 \times 10^3$ cells/well in 16-well Lab-Tek ® chamber slides TM for 24 h, and used for infection at ~75% confluence. Trypomastigotes were harvested, washed with serum-free RPMI containing 1% BSA, and mixed with various concentrations of proteoglycans. After 30 min at 37° C., $5 \times 10^5$ parasites in a total volume of 100 μl were added to each well containing subconfluent cultures of Vero cells and allowed to interact for 2 h at 37° C. At the end of the incubation time, cell monolayers were rinsed three times with serum-free medium, and further incubated in RPMI-1640 containing 1% Nu-serum for 3 days at 37° C. Finally, monolayers were washed, stained with Diff-Quik ®, and examined under a microscope to estimate the ratio of infected (i.e., Vero cell containing more than one intracellular amastigote) to non-infected Vero cells. In order to establish if the inhibitory effect was due to interaction of heparin and heparan sulfate with trypomastigotes rather than to Vero cells, parasites or host cells were preincubated with the putative inhibitors, washed extensively, and assayed for infection as above.

Figure 4:
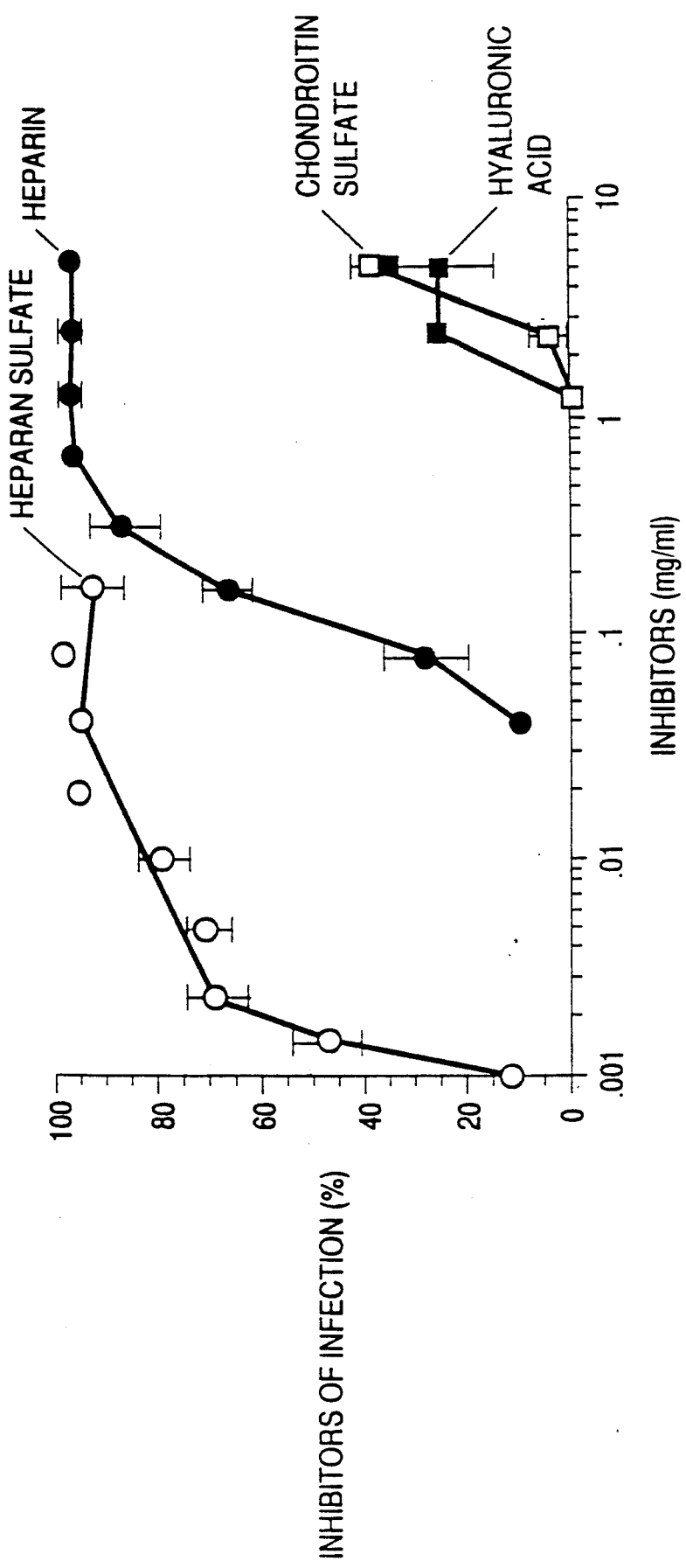

Referring to FIG. 4, heparan sulfate (open circles) was found to be a potent inhibitor of infection, causing a 50% reduction at 1.5 μg/ml. Heparin (filled circles) reduced infection by 50% at 100 μg/ml. Chondroitin sulfate (open squares) and hyaluronic acid (filled squares) had little effect on infection even at high concentrations.

Isolation and Identification of Penetrin

Because it appeared that the protein mediating trypomastigote binding to fibroblasts is a heparin binding protein, a heparin-Sepharose column was used in an attempt to purify the T. cruzi factor.

The trypomastigotes were first [$^{125}$I]-labeled Tissue culture trypomastigotes were washed three times by centrifugation as above and their surface proteins labeled by Iodo-gen TM (1,3,4,6-tetrachloro-3a,6a-diphenylglycoluril) catalyzed iodination as described (Howard et al., J. Protozool. 29:114, 1982; Markwell, Anal. Biochem. 125:427, 1982). Briefly, washed parasites were resuspended at $10^8$ cells/ml in cold PBS and added to glass vials coated with Iodo-gen TM. Then, 500 μCi of carrier-free [$^{125}$I] were added and the suspension incubated 15 min on ice with intermittent agitation. To stop the reaction, the parasite suspension was transferred to a 15 ml conical tube and washed three times in cold PBS, pH 7.2. Alternatively, parasites were labeled with Iodo-beads TM (N-chloro-benzenosulfomide sodium salt, Pierce Chemical Co., Rockford, Ill., using 4 beads (1.2 μmoles) and 500 μCi of carrier-free [$^{125}$I]. After 15 min on ice, parasites were removed and washed as above.

For purification of the heparin binding protein, [125I]-surface labeled trypomastigotes ($2.5 \times 10^8$) were lysed by sonication, unbroken cells nuclei and debris were removed by low speed centrifugation ($100 \times g$, 5 min) and membranes were isolated by ultracentrifugation ($100,000 \times g$, 1h), washed twice with PBS and then lysed in a solution containing 1% Triton X-100 and an anti-protease cocktail (10mM pepstatin, 10mM leupeptin, 10mM iodoacetamide, 10 μg/ml soybean trypsin inhibitor, and 2mM PMSF) for 1 h on ice. Soluble membrane proteins were isolated by centrifugation at $15,000 \times g$ for 30 min at 4° C. and immediately mixed with an equal volume of heparin-Sepharose. After overnight incubation at 4° C. with gentle shaking, heparin-Sepharose, along with bound material, was removed by centrifugation ($175 \times g$ for 10 min; at 4° C.), resuspended in PBS, poured into a column ($0.8 \times 4$ cm) and washed with 0.05% Triton X-100 in PBS, pH 7.2 until radioactivity in the effluent Was background levels (i.e., <100 cpm/100 μl ). Finally, bound proteins were eluted by stepwise addition of 25 ml of 0.25M, 0.5M, 1.0M and 3.0M NaCl, 1.5M guanidine-HCl and 2.0 M potassium thiocyanate; for each addition, 2-ml fractions were collected. The radioactivity of the eluted fractions was monitored on a gamma counter, and fractions corresponding to the radioactive peaks pooled, dialyzed extensively against 200mM ammonium bicarbonate and lyophilized. A single sharp peak of [$^{125}$I]-labeled protein was eluted by 1.0M NaCl. Further washing with 3.0M NaCl, 1.5M guanidine-HCl and 2.0M potassium thiocyanate did not elute further [$^{125}$I]-labeled material. Based on the radioactivity applied to the column (75% of which was TCA precipitable) and radioactivity recovered in the 1.0M NaCl peak, the eluted material represents ~4.1% of labeled surface proteins.

Figure 5:
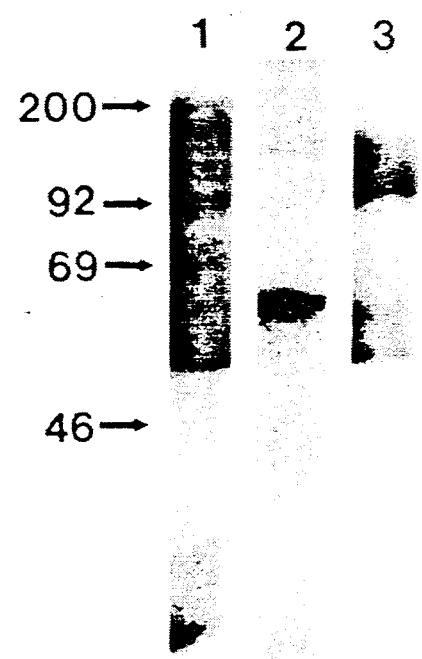

Analysis of the 1.0M NaCl eluate by SDS-PAGE and autoradiography revealed a single 60 kD band (FIG. 5, lane 2), whose mobility in the polyacrylamide gel was not changed by reduction with 2% 2-mercaptoethanol.

A 60 kD heparin-binding protein was similarly isolated from trypomastigotes that had been endogenously labeled with $^{35}$S]-methionine. An additional band of 32 kD was inconsistently observed in the 1.0M NaCl eluate and its absence or relative abundance was not altered by reducing agents. Also, antibody to the 60 kD protein sometimes recognized a 32 kD band in trypomastigote lysates. Furthermore, when the 32 kD band was present in the 1M NaCl eluate, it clearly bound heparin as judged by various binding assays. Therefore, the 32 kD band appears to be a degradation product of the 60 kD polypeptide.

Figure 6:
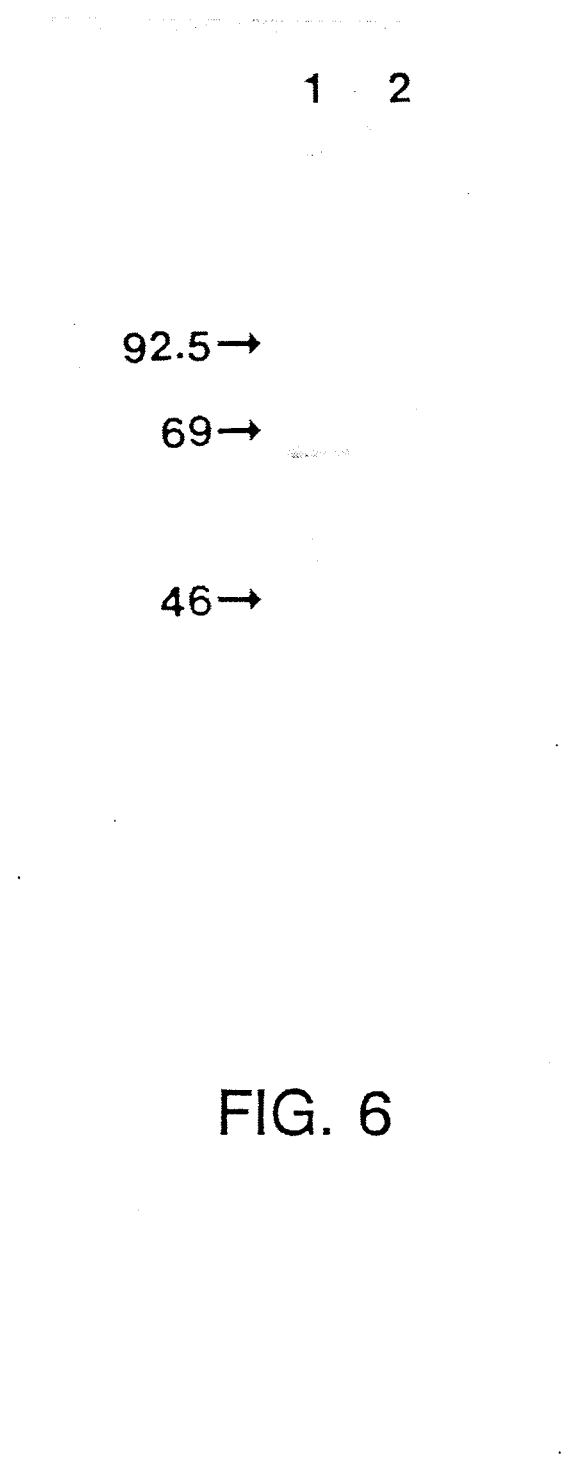

Non-infective epimastigotes, unlike infective trypomastigotes, did not adhere to plastic surfaces coated with proteoglycans. Consistent with this observation, the 60 kD heparin-binding protein found in trypomastigotes was not detectable in epimastigotes. Furthermore, antibodies raised against the 60 kD protein (described below) did not react with amastigote lysates by immunoblot (FIG. 6, lane 2). The 60 kD surface protein is therefore developmentally regulated. It was named penetrin, on the basis of the experiments described below.

Penetrin Binds to Fibroblasts by a Receptor-Ligand Interaction

Figure 7:
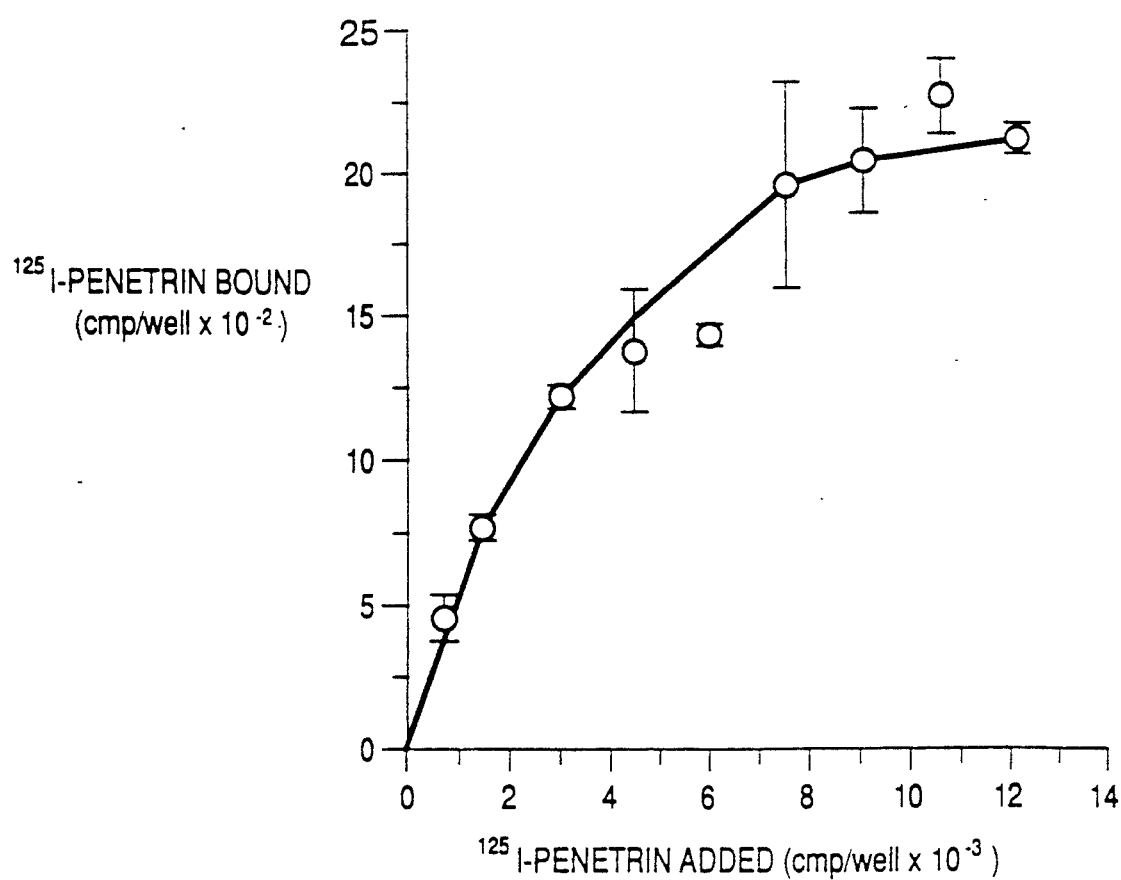
FIG. 7 is a graphical representation of the effect of several proteoglycans on binding of [$^{125}$I]-labeled column-purified penetrin to heparin-Sepharose.

To determine if [$^{125}$I]-labeled penetrin was still active in binding extracellular matrix proteins after isolation by heparin affinity chromatography, rebinding and inhibition of rebinding to heparin-Sepharose beads was performed. Briefly, column purified [$^{125}$I]-labeled penetrin was incubated with or without compounds and mixed with 100 μl of heparin-Sepharose. The mixture was incubated at room temperature for 2 h under slow rocking. The slurry was then centrifuged (500×g, 5 min), washed three times with PBS, and bound radioactivity determined in a gamma counter. Referring to FIG. 7, in the absence of competitors, column-purified [$^{125}$I]-labeled penetrin retained its ability to bind heparin-Sepharose.

For inhibition experiments, an aliquot of the purified heparin-binding protein was mixed with putative inhibitors for 1 h at room temperature, and the mixture added to 100 μl of heparin-Sepharose as above. The amount of [$^{125}$I]-labeled protein retained by the agarose beads was assessed by elution of the protein with 1% SDS, SDS-polyacrylamide gel electrophoresis and autoradiography, and quantitated in a laser scanning densitometer (Pharmacia LKB, Ultroscan XL). One hundred percent binding was taken as the amount of protein retained by the heparin-Sepharose in the absence of added inhibitor. Referring to Table 2, adsorption of penetrin was inhibited by pre-incubation with soluble heparin, heparan sulfate or collagen, but not with other glycosaminoglycans (chondroitin sulfate and hyaluronic acid). Glycoproteins such as bovine submaxillary mucin, hog gastric mucin, and fetuin did not affect penetrin binding. Consistent with the conclusions derived from the binding of viable parasites to proteoglycans (FIG. 1), re-binding of penetrin to heparin-Sepharose was also inhibited by collagen, which was as good an inhibitor as heparin and heparan sulfate.

TABLE 2

| Effect of Various Compounds on Binding of Column-Purified Penetrin to Heparin-Sepharose | |
|---|---|
| Compound (100 μg/ml) | Penetrin Bound (cpm × $10^{-3}$) |
| Bovine Serum Albumin | 1.9 |

TABLE 2-continued

| Effect of Various Compounds on Binding of Column-Purified Penetrin to Heparin-Sepharose | |
|---|---|
| Compound (100 μg/ml) | Penetrin Bound (cpm × $10^{-3}$) |
| Heparin | 0.7 |
| Heparan Sulfate | 0.75 |
| Chonodroitin Sulfate | 1.6 |
| Hyaluronic Acid | 1.8 |
| Collagen | 0.6 |

Penetrin was biologically active, as it bound to subconfluent monolayers of Vero cells. Binding of the [$^{125}$I]-labeled protein to Vero cell monolayers was dose dependent and saturable, and it was inhibited by heparin, heparan sulfate and collagen, but not by chondroitin sulfate and hyaluronic acid. The inhibition pattern was similar to that in the above-described heparin-Sepharose was used as a binding probe, or to the profile of trypomastigote binding to matrices coated with heparin and other extracellular matrix proteins. Therefore, the binding specificity of the isolated penetrin reproduces the binding characteristics of intact trypomastigotes.

Binding of [$^{125}$I]-labeled penetrin to Vero cells was assayed as follows. Vero cells, grown in multiwell plates to confluence as described above, were rinsed once with 1% BSA-RPMI-1640, and incubated at 37° C. with increasing concentrations of [$^{125}$I]-labeled penetrin. After 1 h the medium was removed, cell monolayers were washed three times with PBS, solubilized with 100 μl of 2M NaOH, and the retained radioactivity measured in a gamma counter. For inhibition experiments, an aliquot of [$^{125}$I]-labeled penetrin was preincubated with the potential inhibitors prior to adding to confluent cells, and processed as above.

Referring to Table 3, heparin, collagen, and heparan sulfate, but not chondroitin sulfate inhibited binding of [$^{125}$I]-labeled penetrin to fibroblasts.

TABLE 3

| Effect of Various Compounds on Binding of Column-Purified Penetrin to Fibroblasts | | |
|---|---|---|
| Compound | Concentration (μg/ml) | % Inhibition |
| Heparin | 0 | 0 |
|  | 5 | 25 |
|  | 25 | 55 |
|  | 50 | 75 |
|  | 100 | 89 |
|  | 250 | 91 |
| Collagen | 100 | 60 |
|  | 250 | 95 |
| Heparan Sulfate | 250 | 65 |
| Chondroitin Sulfate | 250 | 12 |

Cloning of Penetrin

A *T. cruzi* trypomastigote (Silvio X-10/4) genomic library in λZAP was screened with antisera monospecific for penetrin. Antisera were produced in C3H mice after three or more injections (10 days apart), in incomplete Freund's adjuvant, of affinity purified penetrin, or of the 60 kD penetrin band cut-out from the polyacrylamide gel after SDS-PAGE. The penetrin antibodies reacted with a 60 kD polypeptide in lysates of trypomastigotes, as determined by immunoblots and immunoprecipitation of [$^{35}$S]-methionine labeled parasites. The antibody also immunoprecipitated penetrin labeled with $^{125}$I after surface iodination of trypomastigotes with Iodobeads. Ten DNA clones in *E. coli* XI-1

Blue (Short et al., *Nucl. Acids. Res.* 16:7583, 1988) were identified with this antibody by standard techniques. Bacterial lysates, after SDS-PAGE and transfer to nitrocellulose, revealed a band of 62 kD recognized by the penetrin antibody. The size of recombinant penetrin was therefore close to endogenous penetrin (60 kD). Recombinant penetrin, like its endogenous counterpart, is a heparin-binding protein, as it was retained by heparin-Sepharose columns and was eluted at 1M NaCl.

Adherence of Fibroblasts to Endogenous and Recombinant Penetrin

If penetrin binds to a specific receptor(s) on the surface of mammalian cells, then it is possible that the binding will promote cell adherence to the substratum, analogous to the property of some mammalian adhesive proteins, including fibronectin and vitronectin. This possibility was tested by determining if polystyrene wells that had been coated with penetrin would provide a substratum for Vero cell adhesion and spreading.

Various concentrations of endogenous and recombinant penetrin, or of fibronectin, all diluted in PBS (pH 7.2), were used to coat 96-well microtiter plates by incubation overnight at 4° C. After washing with PBS, wells were blocked with 1% heated BSA (60 min at 56° C.) in PBS for 2 h at room temperature, washed two times with PBS and incubated at 37° C. with 1% BSA, RPMI 1640 medium until needed. To assay for cell attachment, Vero cells were dispersed from confluent monolayers in Hanks' balanced salt solution (Gibco, 310-4180AG), containing 10mM EDTA, washed three times with RPMI 1640 medium and resuspended in methionine-free medium. After 30 min at 37° C., 50 $\mu$Ci/ml [$^{35}$S]-methionine were added (New England Nuclear, Boston, Mass.) and incubated for 1 h at 37° C. Cells were washed thrice in RPMI 1640 medium and resuspended at $10^6$ cells/ml in RPMI 1640 medium containing 1% BSA. Aliquots of [$^{35}$S]-methionine-labeled Vero cells were added to each well and incubated at 37° C. After appropriate incubation times, the wells were washed by gently aspirating the culture medium, and adding 100 $\mu$l warm RPMI 1640. Cells that remained attached after two washes were solubilized by addition of 100 $\mu$l of 2N NaOH and counted by liquid scintillation. In selected assays, attached cells were visualized after fixation with 4% paraformaldehyde and staining with Diff-Quik. The results showed that after adhering to matrices coated with penetrin, Vero cells lost their round form and spread, as did the cells in fibronectin-coated wells. In contrast, no adherence and spreading of cells occurred in the wells coated with BSA.

Figure 8:
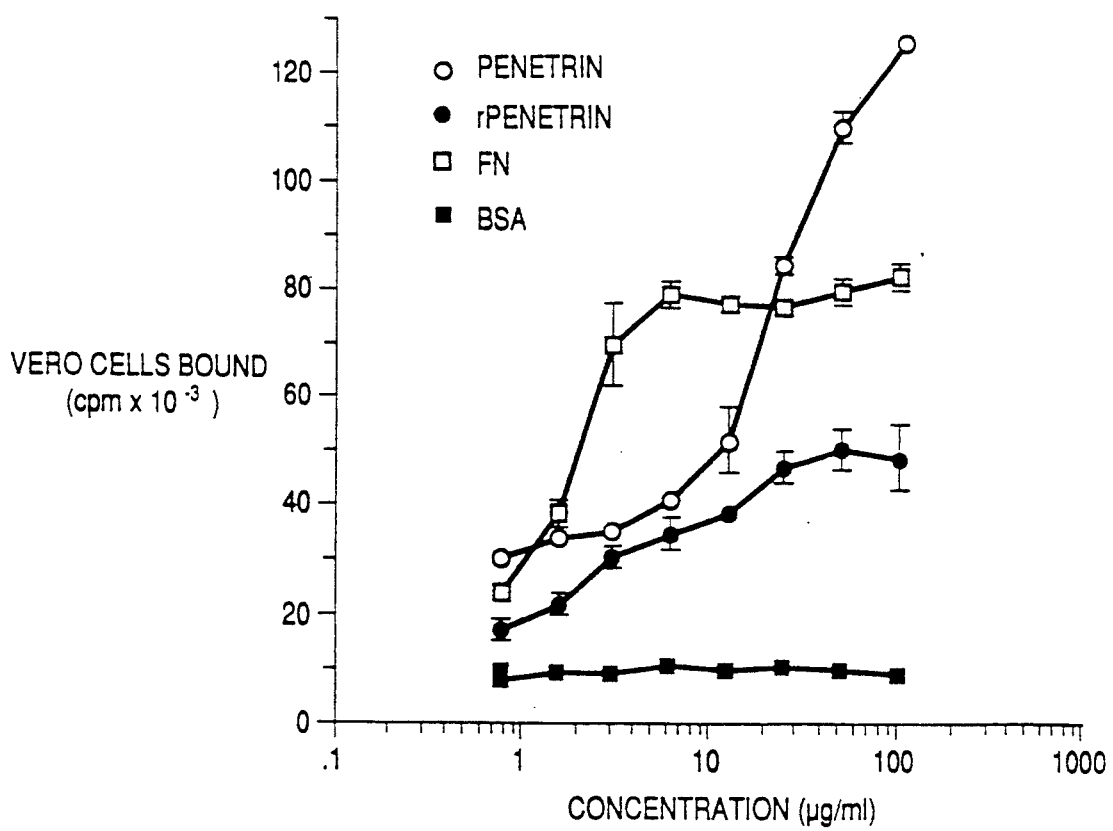
FIG. 8 is a graphical representation of the effect of the concentration (μg/ml) of penetrin (open circles), recombinant penetrin (filled circles), fibronectin (squares with central dot), BSA (x) used to coat polystyrene wells on the adherence of Vero cells (cpm $\times 10^{-3}$)

Referring to FIG. 8, Vero cell adherence to penetrin (open circles) was dose-dependent, and interestingly, more efficient than adherence to fibronectin (squares with central dot) at concentrations higher than 20 $\mu$g/ml. Attachment of fibroblasts to penetrin was confirmed by using polystyrene wells coated with recombinant penetrin (filled circles) expressed in *Escherichia coli*. Recombinant penetrin, like its endogenous counterpart, promoted attachment of fibroblast to the substratum and spreading, although it was somewhat less effective than endogenous penetrin. BSA (x) did not promote adherence.

Inhibition of *T. cruzi* Infection by Penetrin

That penetrin mediates T. cruzi invasion of host cells was demonstrated by a series of experiments showing that soluble endogenous penetrin inhibits infection. For this experiment subconfluent monolayers of Vero cells were preincubated with penetrin or heparin for 30 min followed by incubation with trypomastigotes ($5 \times 10^5$) for 3 h in the presence of various concentrations of penetrin, washed with RPMI to remove unbound parasites (and penetrin), and incubated for 3 d at 37° C. to allow *T. cruzi* to differentiate and replicate inside the host Vero cells. Monolayers were washed, stained with Diff-Quik ®, and examined under a microscope to estimate the ratio of infected (i.e., Vero cells containing more than one intracellular amastigote) to non-infected Vero cells.

Figure 9:
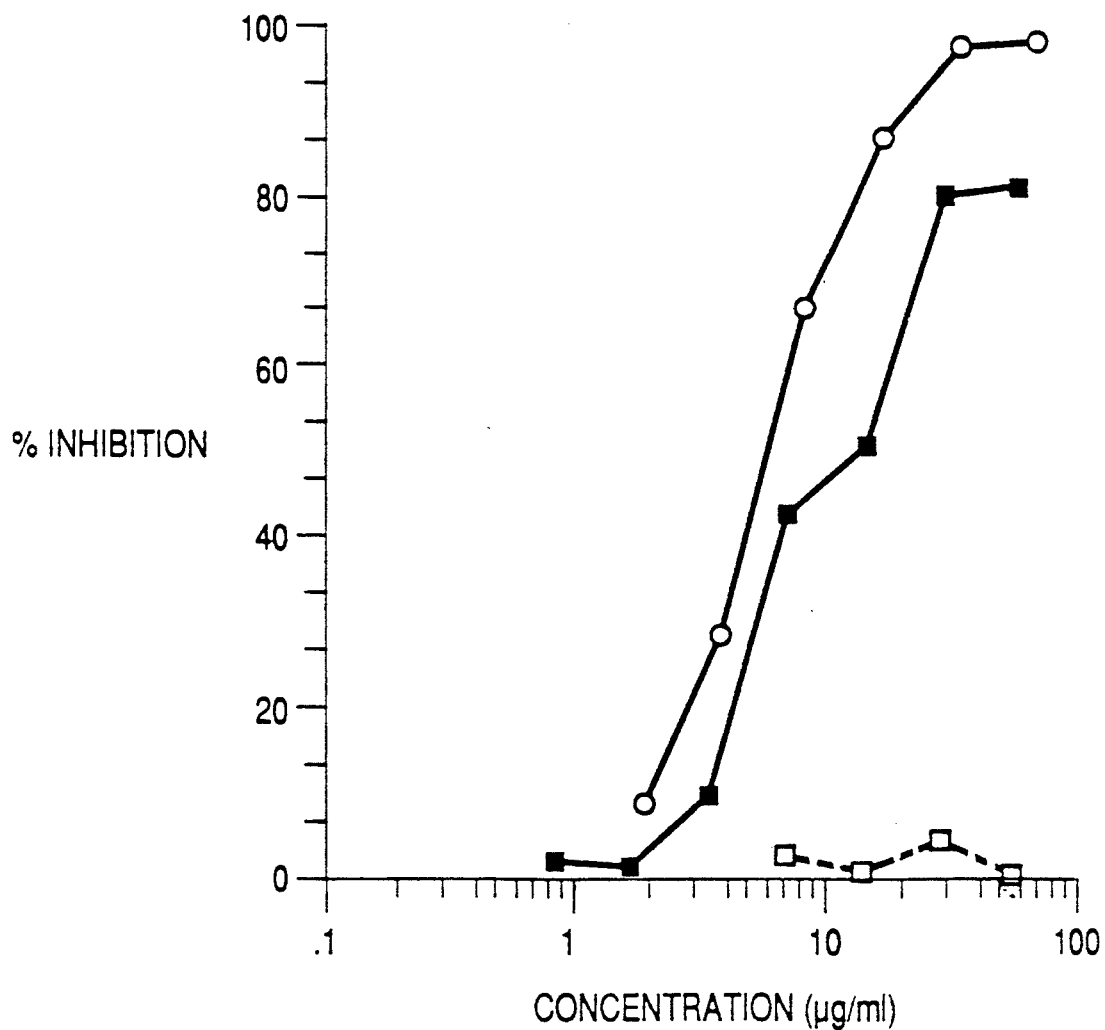
FIG. 9 is a graphical representation of the effect of the concentration (μg/ml) of penetrin (filled squares), heparin (open circles), or heparin-Sepharose depleted penetrin (open squares) on trypomastigote infection (% inhibition) of Vero cells.

Referring to FIG. 9, *T. cruzi* infection was effectively blocked by penetrin (filled squares) in a saturable manner, with concentration as low as 3 $\mu$g/ml producing a detectable degree of inhibition. The dose-response curve produced by the *T. cruzi* protein was comparable to that of the penetrin-binding proteoglycan, heparin (open circles). The effect of penetrin on infection was completely abrogated by adsorption of the protein to heparin-Sepharose (open squares) in agreement with the property of penetrin to bind heparin. This adsorption was accomplished by applying penetrin at the indicated concentration to a heparin-Sepharose column and concentrating the effluent.

Penetrin Mediated Entry of *E. coli* into Fibroblasts

*E. coli* expressing penetrin are able to enter non-phagocytic mammalian cells which normally exclude *E. coli*. This was demonstrated using *E. coli* XL-1 Blue transferred with clone HBP-6, that expresses penetrin; clone 7F, that does not express penetrin but does express *T. cruzi* neuraminidase; or Bluescript. Recombinant bacteria were grown overnight at 37°, washed twice in PBS, resuspended at $10^8$ cells/ml, and aliquots of $2 \times 10^7$ *E. coli* were added to monolayers of $2 \times 10^5$ Vero cells per microliter well in 1 ml of RPMI 1640 medium containing 1% BSA. Bacteria were centrifuged onto the cell monolayer, and the cultures were incubated at 37° for 3 h in a 5% $CO_2$/95% air atmosphere, washed three times with sterile PBS, and incubated for an additional 1.5 h at 37° C. in RPMI 1640 medium containing 1% BSA and 75 $\mu$g/ml gentamicin (to kill bacteria bound to outer membrane). The monolayers were then washed three times in sterile PBS, and lysed with 0.5% Triton X-100 in deionized water to release internalized bacteria, which were quantitated in agar plates. For inhibition of bacterial entry, *E. coli* cells were preincubated with 250 $\mu$g/ml of the putative inhibitors in 1 ml of RPMI 1640, 1% BSA, added to each well of the monolayer and invasion quantitated by gentamicin-resistant viable bacteria as above.

The clone expressing penetrin was very effective in entering *E. coli*, whereas *E. coli* expressing the *T. cruzi* neuraminidase or transformed with pBluescript were not. An average of 4.3% of the penetrin-expressing *E. coli* that were added to the fibroblast monolayer survived the antibiotic treatment. Further, the same extracellular matrix proteins that reacted with intact *T. cruzi* and with isolated penetrin were also effective in preventing *E. coli* entry into Vero cells. Thus, collagen type IV at 250 $\mu$g/ml completely abrogated penetration of the bacteria in mammalian cells (<0.001% survival) and heparin and heparan sulfate, at the same concentration, inhibited penetration by 85% (0.6% survival). Chondroitin sulfate and hyaluronic acid were without effect in the assay. *E. coli* transformed with the *T. cruzi* neuramidase gene or XL1-Blue alone could not The ability of *E. coli* HBP-6 to penetrate Vero cells was confirmed by transmission electron microscopy. The invasion assay was performed as described above, except that $8 \times 10^7$ bacteria were added to $8 \times 10^5$ Vero cells in tissue culture wells (Falcon, 6-well plates). The samples were then fixed, embedded, sectioned and stained as described by Isberg et al. (*Nature* 317:262, 1985). Infected monolayers were fixed with 2% glutaraldehyde and 2% osmium tetroxide in 0.1M cacodylate buffer (pH 7.4) and stained with uranyl acetate. Samples were dehydrated with ethanol, embedded in Epon, thin sectioned, and poststained with uranyl acetate and lead acetate.

Microscopy of Vero cells exposed to *E. coli* transformed with clone HBP-6 revealed bacteria in direct contact with the outer membrane of fibroblasts or intracellularly. In contrast, no bacteria were found inside Vero cells exposed to *E. coli* transformed with clone 7F. Most intracellular bacteria were not surrounded by host cell membranes, but instead were in direct contact with the cytosol.

To determine if HBP-6 bacteria would replicate inside the Vero cells, monolayers were incubated at 37° C. for an additional 18 h in the presence of gentamicin, and surviving bacteria were quantitated either by the agar plate technique or electron microscopy. No evidence of intracellular multiplication of the bacteria was noted. The presence of intracellular bacteria did not produce any obvious morphological alteration in the infected culture cells. Likewise, the intracellular bacteria were morphologically normal and alive, as judged by their ability to form colonies on agar after being released from the fibroblasts by detergent lysis. In addition, if the gentamicin-containing medium was replaced with antibiotic-free medium, *E. coli* HBP-6 grew abundantly in the culture supernatant after overnight incubation at 37° C., whereas similar antibiotic replacement did not produce bacterial growth in the monolayers that had been exposed to *E. coli* transformed with clone 7F or with *E. coli* transformed with pBluescript. These results suggest that intracellular bacteria capable of expressing penetrin can be released into the medium.

If penetration of Vero cells by *E. coli* transformed with clone HBP-6 is mediated by penetrin, then the recombinant *T. cruzi* protein should be exposed on the surface of the bacteria. This prediction was confirmed by indirect immunofluorescence (Leong et al., *EMBO J.* 9:1979, 1990), which revealed a bright fluorescence of intact, viable bacteria, produced by anti-penetrin antibodies. Penetrin antibodies did not react with *E. coli* transformed with clone 7F, nor did normal sera bind to intact *E. coli* transformed with clone HBP-6. It is of interest to note that only about 10% of HBP-6 bacteria were recognized by the penetrin antibodies, close to the proportion of bacteria (4.3%) that invaded the Vero cell monolayer. This finding provides further support for the argument that the invasive bacterial phenotype is represented by the bacterial subpopulation recognized by the penetrin antibodies.

For the experiments described above, heparin, heparan sulfate, chondroitin sulfate, hyaluronic acid, collagens type I and IV, bovine serum albumin, cyanogen bromide, Sepharose ® CL-4B-200, and phenylmethylsulfonyl fluoride (PMSF) were purchased from Sigma Chemical Co., St. Louis, Mo. Iodine$^{125}$ (892 mCi/ml) was from ICN Radiochemicals, Irvine, Calif. Iodogen ™ and Iodo-beads ™ were obtained from Pierce Chemical Co., Rockford, Ill. All culture reagents were obtained from Gibco Laboratories (Grand Island, N.Y.). Heparin was coupled to cyanogen bromide-activated Sepharose ® CL-4B as described (March et al., *Anal. Biochem.* 60:149, 1974).

Antibodies

Antibodies directed against penetrin can be used to diagnostically to detect *T. cruzi* in a sample of biological fluid. Such antibodies can be produced using intact penetrin or immunogenic fragments thereof. The portion of penetrin whose DNA and amino acid sequences are presented in SEQ ID NO: 1 and SEQ ID NO: 2 respectively may be useful for preparation of antibodies. Because this portion of penetrin is adjacent to a hydrophobic region and is relatively hydrophilic, it may be exposed on the surface of *T. cruzi* The deduced amino acid sequence of penetrin can be analyzed to locate regions that are likely to be immunogenic using methods described in *Current Protocols in Immunology* (Coligan et al. (eds.) Greene Publishing Associates and John Wiley & Sons, Inc., New York, 1991). Antibodies can be produced and used in an ELISA assay or other standard assay format according to standard procedures well known to those in the art (*Current Protocols in Immunology,* Coligan et al. (eds.) Greene Publishing Associates and John Wiley & Sons, Inc., New York, 1991).

Penetrin, or immunogenic fragments thereof, can be used in various immunological assays to detect the presence of anti-penetrin antibodies in the bodily fluids of patients suspected of being infected with *T. cruzi.* Methods for detecting antibodies using a protein or fragment thereof are described in *Current Protocols in Immunology* (Coligan et al. (eds.) Greene Publishing Associates and John Wiley & Sons, Inc., New York, 1991).

Therapy

Since penetrin binds to heparin proteoglycans such as, heparan sulfate, heparin, and derivatives of heparin lacking anti-clotting properties, can be used to interfere with trypomastigote infection of cells within a human patient. Penetrin itself, or infection inhibiting fragments thereof, may be used to interfere with trypomastigote infection of cells within a human patient.

The following infection inhibition assay can be used to determine if a particular penetrin fragment, or heparin derivative, inhibits *T. cruzi* invasion of host cells. Briefly, subconfluent monolayers of Vero cells are preincubated with the candidate compound for 30 min followed by incubation with trypomastigotes ($5\times10^5$) for 3 h in the presence of various concentrations of the candidate compound, washed With RPMI to remove unbound parasites (and candidate compound), and incubated for 3 d at 37° C. to allow *T. cruzi* to differentiate and replicate inside the host Vero cells. Monolayers are washed, stained with Diff-Quik®, and examined under a microscope to estimate the ratio of infected (i.e., Vero cell containing more than one intracellular amastigote) to non-infected Vero cells.

These compounds can be administered in an effective amount either alone or in combination with a pharmaceutically acceptable carrier or diluent. All of the suitable compounds or compositions can be administered alone or in combination with other therapeutic agents. They may be administered by any convenient means, e.g., intravenously, intramuscularly, subcutaneously or intranasally. The compounds can be effective whether administered during the acute of chronic phase of infection. Dosage will generally be in the range of 1 to 100 µg/ml per kilogram of body weight.

Penetrin, preferably recombinant, or immunogenic fragments thereof may be used in a vaccine composition to vaccinate those at risk for becoming infected with *T. cruzi* Vaccine compositions may include penetrin (or fragments thereof) stabilizers, antibiotics and a pharmaceutically carrier.

Use

Penetrin can be used to coat solid support surfaces (e.g., tissue culture plates or hollow fibers) for growing eukaryotic to provide a surface that promotes attachment and spreading of the eukaryotic cells.

Deposit

Plasmid HBP-6 has been deposited with the American Type Culture Collection on Oct. 17, 1991 and bears the accession number ATCC No. 75126. Applicants' assignee, New England Medical center Hospitals, Inc., acknowledges its responsibility to replace this deposit should this deposit die before the end of the term of a patent issued hereon, and its responsibility to notify the ATCC of the issuance of such a patent, at which time the deposit will be made available to the public. Prior to that time the deposit will be made available to the Commissioner of Patents under the terms of 37 CFR Section 1.14 and 35 USC Section 112.

We claim:

1. A substantially pure nucleic acid consisting of a nucleotide sequence set forth as SEQ ID NO: 1.

2. A substantially pure nucleic acid consisting of a nucleotide sequence that encodes the protein set forth as SEQ ID NO: 2.

3. A plasmid comprising the nucleic acid of claim 1 or claim 2.

4. The plasmid of claim 3, said plasmid further comprising an expression control sequence capable of directing expression of said penetrin polypeptide.

5. A cell comprising the nucleic acid of claim 1 or claim 2.

6. The cell of claim 5 wherein said cell is a prokaryotic cell.

7. The cell of claim 5 wherein said cell is a eukaryotic cell.

8. The cell of claim 7 wherein said cell is mammalian cell.

9. The DNA molecule identified as HB6, deposited with the ATCC under accession number 75126.

* * * * *

UNITED STATES PATENT AND TRADEMARK OFFICE
CERTIFICATE OF CORRECTION

PATENT NO.   : 5,322,936

DATED        : June 21, 1994

INVENTOR(S)  : Miercio E.A. Pereira and Eduardo Ortega-Barria

It is certified that error appears in the above-identified patent and that said Letters Patent is hereby corrected as shown below:

On the title page, item [56] References Cited, under U. S. Application Data", replace "October 17, 1993" with --October 17, 1991--;

Column 1, line 9, replace "October 17, 1993" with --October 17, 1991--;

Column 2, line 16, replace "at lest" to --at least--;

Column 2, line 20, replace "HBD-6" with --HBP-6--;

Column 2, line 47, replace "HBp-6" with --HBP-6--;

Column 3, line 52, replace "acido" with --acid--;

Column 3, line 52, replace "acid" with --acids--;

Column 9, line 3, replace "$^{35}$S]-methionine" with --[$^{35}$S]-methionine;

Column 13, line 2, after "could not", add the following: "penetrate (0.003% and 0.002% survival respectively)."

UNITED STATES PATENT AND TRADEMARK OFFICE
CERTIFICATE OF CORRECTION

PATENT NO. : 5,322,936
DATED : June 21, 1994
INVENTOR(S) : Miercio E.A. Pereira and Deuardo Ortega-Barria It is certified that error appears in the above-indentified patent and that said Letters Patent is hereby corrected as shown below:

Columns 15-16, "Sequence Listing", under "(1) General Information, add the following:

(ii) TITLE OF INVENTION: Nucleic Acids Encoding Trypanosoma Cruzi Heparin-Binding Protein.

Signed and Sealed this

Eleventh Day of October, 1994

Attest:

BRUCE LEHMAN

*Attesting Officer*    *Commissioner of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
( A ) LENGTH: 394
( B ) TYPE: nucleic acid
( C ) STRANDEDNESS: single
( D ) TOPOLOGY: linear ( x i ) SEQUENCE DESCRIPTION: SEQ ID NO: 1:

```
GCT GCA CAT CGT CGT CCA CCG GCA ACA CAT TTA GTG ATG CGC TGC   45
TCA GCC CGG AGG TGT GTT TCC ACC GCA CAC GAA CAT CAC GAT CAG   90
TGG GAA CCG CTT CAC GGT CAC GAG GCC GAT CCC TCG GTC GGG TTT  135
GGT CCT TTG GGG CCC GTC GTG TGT CGC GAT GAA TGG ACT GGC GAT  180
CAG CAA CGA CTC CGC AGT GGT GCT GAG TGG CAA TGT GTT TCA CGC  225
CGT GGC GCA TCG TCA AGC GTC ATT TAC TTT GTT GGA TTT GCG CTG  270
AGG GTG TCG TGG CAC TCC GTG TTT GCG GTG ATG GGC AAC ACG TTT  315
CAT GTG GCT GGC GCT AAC AGT AGC GCT ATA ACT CTT GAG GGG TCT  360
AGC AGT ACT TTA CCT GAT TGT GCT GAC ACT CGT C                394
```

( 2 ) INFORMATION FOR SEQ ID NO: 2:

( i ) SEQUENCE CHARACTERISTICS:
( A ) LENGTH: 131
( B ) TYPE: amino acid
( D ) TOPOLOGY: Not Relevant ( x i ) SEQUENCE DESCRIPTION: SEQ ID NO: 2:

```
Ala Ala His Arg Arg Pro Pro Ala Thr His Leu Val Met Arg Cys
                5                   10                  15
Ser Ala Arg Arg Cys Val Ser Thr Ala His Glu His His Asp Gln
                20                  25                  30
Trp Glu Pro Leu His Gly His Glu Ala Asp Pro Ser Val Gly Phe
                35                  40                  45
Gly Pro Leu Gly Pro Val Val Cys Arg Asp Glu Trp Thr Gly Asp
                50                  55                  60
Gln Gln Arg Leu Arg Ser Gly Ala Glu Trp Gln Cys Val Ser Arg
                65                  70                  75
Arg Gly Ala Ser Ser Ser Val Ile Tyr Phe Val Gly Phe Ala Leu
```

```
                80                        85                         90
Arg Val Ser Trp His Ser Val Phe Ala Val Met Gly Asn Thr Phe
                95                       100                        105
His Val Ala Gly Ala Asn Ser Ser Ala Ile Thr Leu Glu Gly Ser
                   110                       115                    120
Ser Ser Thr Leu Pro Asp Cys Ala Asp Thr Arg
                   125                       130
```